United States Patent
Köhle et al.

(10) Patent No.: US 7,229,958 B2
(45) Date of Patent: Jun. 12, 2007

(54) FRAGRANCE ALCOHOL-RELEASING POLYSILOXANE

(75) Inventors: Hans-Jürgen Köhle, Mainhausen (DE); Thomas Salomon, Bad Soden-Salmünster (DE); Ronald Smith, Chesterfield, VA (US)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/447,084

(22) Filed: Jun. 6, 2006

(65) Prior Publication Data

US 2007/0021319 A1    Jan. 25, 2007

Related U.S. Application Data

(60) Provisional application No. 60/688,695, filed on Jun. 9, 2005.

(30) Foreign Application Priority Data

Jun. 10, 2005  (DE) .................... 10 2005 026 796

(51) Int. Cl.
    *C11D 3/50*   (2006.01)
(52) U.S. Cl. .................... 510/475; 510/101; 512/1
(58) Field of Classification Search ................ 510/107, 510/475; 512/1
    See application file for complete search history.

(56) References Cited

U.S. PATENT DOCUMENTS 4,524,018 A    6/1985  Yemoto et al.

6,486,333 B1   11/2002  Koichi et al.

FOREIGN PATENT DOCUMENTS

| DE | 3527974    | 2/1987  |
| DE | 197 50 706 | 5/1998  |
| EP | 0 752 465  | 1/1997  |
| EP | 0 799 885  | 10/1997 |
| EP | 0 878 497  | 11/1998 |
| EP | 0 982 023  | 3/2000  |
| EP | 1 099 689  | 5/2001  |
| GB | 2 319 527  | 5/1998  |
| JP | 07-179479  | * 7/1995 |
| JP | 2001-278981 | * 10/2001 |
| JP | 2001-278982 | * 10/2001 |

OTHER PUBLICATIONS

English language abstract of DE 197 50 706, no date.
English language abstract of DE 3527974, no date.

* cited by examiner

*Primary Examiner*—John R. Hardee
(74) *Attorney, Agent, or Firm*—Michael A. Sanzo; Law Office of Michael A. Sanzo, LLC

(57) ABSTRACT

Organopolysiloxanes which contain a fragrance alcohol Y—OH bonded via a betaine ester group having the structure —$N^+R^1R^2$—$CH_2$—C(O)OY, cleave off the fragrance alcohol under acid conditions and are resistant to hydrolysis in the neutral and weakly basic range. The organopolysiloxanes adhere to textile fibres, skin or hair and are suitable as perfume components for textile treatment agents and personal care products.

9 Claims, No Drawings

FRAGRANCE ALCOHOL-RELEASING POLYSILOXANE

CROSS REFERENCE TO RELATED APPLICATIONS

The present application claims priority to German application no. 10 2005 026 796.3, filed on Jun. 10, 2005. This application also claims priority to, and the benefit of, U.S. provisional application 60/688,695, filed on Jun. 9, 2005. The contents of these prior applications are hereby incorporated by reference in their entirety.

FIELD OF THE INVENTION

The invention provides organopolysiloxanes from which a fragrance alcohol can be released under acid conditions.

BACKGROUND OF THE INVENTION

For textile treatment agents and personal care products, perfume components are needed which for an extended period adhere to textile fibres, hair or skin, where they release the fragrance substances of the perfume over an extended period and under controlled conditions. Particularly desirable here are perfume components which do not release their fragrance substances until the user of the personal care product or of the item of clothing treated with the textile treatment agent perspires and unpleasant body odours form due to perspiration. Unpleasant body odours are generally formed through bacteria, which break down the constituents of the sweat. In addition to the formation of unpleasantly smelling compounds, this bacterial degradation also leads to acid degradation products. There is therefore a need for perfume components for textile treatment agents and personal care products which contain fragrance substances in bound form and which release them only under acid conditions, such that an intensified perfume effect can be obtained under these conditions to conceal developing body odours.

Betaine esters of fragrance alcohols are known from WO 6/38528 which can be used in detergents, fabric softeners or cleaning agents and adhere to surfaces such as textile fibres. The fragrance alcohol is released from these betaine esters by hydrolysis, the release of the fragrance alcohol taking place only very slowly under acid conditions. The fragrance alcohol is released from the betaine esters only at pH values of 7 or more.

It is also known from WO 97/36978 that betaine esters of fragrance alcohols are resistant to hydrolysis in the acid range and that the fragrance alcohol is released by hydrolysis only at pH values of over 7.

The betaine esters of fragrance alcohols disclosed in EP-A 1 099 689 are also stable in the acid range.

The same pH-dependence of the stability of betaine esters is also known from DE 35 27 974 for betaine esters used as constituents of hair care products.

Alkoxysilanes are known from U.S. Pat. No. 4,524,018 which contain a fragrance alcohol ROH bonded in the form of an Si—O—R group. The fragrance alcohol is slowly released from these compounds. The document contains no disclosure with regard to the pH-dependence of the release of the fragrance alcohols from the alkoxysilanes and the disclosed alkoxysilanes do not remain adhering to textile fibres, skin or hair because they do not display or cannot develop a positive charge.

EP-A 0 982 023 describes polysiloxanes which contain a fragrance alcohol bonded by means of an Si—O—R group and their use as a constituent of cosmetic preparations. The fragrance alcohol is slowly released from the polysiloxanes in the presence of acetic acid. However, the disclosed polysiloxanes do not display adequate adhesion to surfaces having a negative surface charge, such as textile fibres, skin or hair, since they do not display or cannot develop a positive charge.

DESCRIPTION OF THE INVENTION

Surprisingly it has now been found that organopolysiloxanes which contain a fragrance alcohol Y—OH bonded via a betaine ester group having the structure —$N^+R^1R^2$—$CH_2$—$C(O)OY$, cleave off the fragrance alcohol under acid conditions and are unexpectedly resistant to hydrolysis in the neutral and weakly basic range. These organopolysiloxanes also display a good adhesion to textile fibres, skin or hair, which makes them suitable as perfume components for textile treatment agents and personal care products.

The invention therefore provides organopolysiloxanes from which a fragrance alcohol can be released, wherein the organopolysiloxane comprises at least one functional group Z having the structure

wherein
$R^1$, $R^2$ are mutually independently selected from $C_{1-30}$ alkyl and hydroxyethyl,
Y is the radical of a fragrance alcohol Y—OH and
$A^-$ is the anion of a physiologically compatible acid HA.

The invention also provides textile treatment agents and personal care products which contain at least one organopolysiloxane having the aforementioned structure, as well as detergents which contain at least one surfactant and at least one organopolysiloxane having the aforementioned structure and fragranced fabric rinses which contain at least one organopolysiloxane having the aforementioned structure in the form of an aqueous dispersion.

Organopolysiloxanes within the meaning of the invention are compounds containing at least three silicon atoms, which are bonded together by means of Si—O—Si units and in which more than half of the silicon atoms display at least one radical bonded to the silicon atom by a carbon atom. The organopolysiloxanes according to the invention preferably contain from 3 to 200 and particularly preferably from 5 to 100 silicon atoms. In the organopolysiloxanes according to the invention, preferably more than 50% of the silicon atoms have two radicals bonded to the silicon atom by carbon atoms and particularly preferably more than 80%. The radicals bonded to silicon atoms by carbon atoms can be $C_{1-30}$ alkyl radicals, $C_{2-30}$ alkenyl radicals or $C_{6-30}$ aryl radicals, which can display other substituents. The radicals bonded to silicon atoms by carbon atoms are preferably methyl groups or phenyl groups and particularly preferably methyl groups.

The organopolysiloxanes according to the invention comprise at least one betaine ester group having the structure

which is covalently bonded to the polysiloxane and for which
$R^1$, $R^2$ are mutually independently selected from $C_{1-30}$ alkyl and hydroxyethyl,
Y is the radical of a fragrance alcohol Y—OH and A⁻ is the anion of a physiologically compatible acid HA.

In a preferred embodiment of the invention the betaine ester groups are coupled to silicon atoms of the organopolysiloxane via hydroxyethylene bridges and the organopolysiloxane has the structure

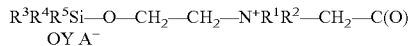
$$R^3R^4R^5Si-O-CH_2-CH_2-N^+R^1R^2-CH_2-C(O)OY\ A^-$$

wherein
$R^3$ is a polysiloxane radical bonded by an oxygen atom,
$R^4$ is a $C_{1-30}$ alkyl group or phenyl,
$R^5 = R^3$ or $R^4$ and
$R^1$, $R^2$, Y and $A^{31}$ have the meaning cited above.

In a particularly preferred embodiment of the invention betaine ester groups are bonded via hydroxyethylene bridges to the terminal silicon atoms of a polydimethyl siloxane having 2 to 300 silicon atoms. In this particularly preferred embodiment the organopolysiloxane has the structure

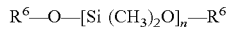
$$R^6-O-[Si(CH_3)_2O]_n-R^6$$

wherein
n=3–200,
$R^6 = -CH_2-CH_2-N^+(CH_3)_2-CH_2-C(O)\ OY\ A^-$ and
Y and A⁻ have the meaning cited above.

Fragrance alcohols Y—OH within the meaning of the invention are all compounds having a fragrance and having a hydroxyl group bonded to a carbon atom, wherein no further atoms apart from hydrogen and carbon are bonded to this carbon atom. The organopolysiloxanes according to the invention preferably contain fragrance alcohols Y—OH in bonded form which are used as constituents of perfume preparations.

The organopolysiloxanes according to the invention particularly preferably contain fragrance alcohols Y—OH in bonded form which are selected from the series comprising 4-allyl-2-methoxyphenol (eugenol), 3-(2-bornyloxy)-2-methyl-1-propanol, 2-tert-butylcyclohexanol, 4-tert-butylcyclohexanol, benzyl alcohol, 1-decanol, 9-decen-1-ol, dihydroterpineol, 2,4-dimethyl-4-cyclohexen-1-yl methanol, 2,4-dimethylcyclohexyl methanol, 2,6-dimethyl-2-heptanol, 2,6-dimethyl-4-heptanol, 3a,4,5,6,7,7a-hexahydro-2,4-dimethyl-4,7-methano[1H]inden-5-ol, 3,7-dimethyl-1,6-nonadien-3-ol, 2,6-dimethyl-2,7-octadien-6-ol (linalool), cis-3,7-dimethyl-2,6-octadien-1-ol (nerol), trans-3,7-dimethyl-2,6-octadien-1-ol (geraniol), 3,7-dimethyl-1,7-octanediol, 3,7-dimethyl-1-octanol (tetrahydrogeraniol), 2,6-dimethyl-2-octanol (tetrahydromyrcenol), 3,7-dimethyl-3-octanol (tetrahydrolinalool), 2,6-dimethyl-7-octen-2-ol (dihydromyrcenol), 3,7-dimethyl-6-octen-1-ol (citronellol), 2,2-dimethyl-3-(3-methylphenyl)-1-propanol, 2,2-dimethyl-3-phenyl-1-propanol, 2-ethoxy-4-methoxymethylphenol, 2-ethyl-4-(2,2,3-trimethyl-3-cyclopenten-1-yl)-2-buten-1-ol, cis-3-hexen-1-ol, 4-(4-hydroxy-3-methoxyphenyl)-2-butanone, 1-hydroxy-2-(1-methyl-1-hydroxyethyl)-5-methyl-cyclohexane, 3-(hydroxymethyl)-2-nonanone, 4-(4-hydroxy-4-methylpentyl)-3-cyclohexene-1-carboxaldehyde, isoborneol, 3-isocamphylcyclohexanol, 2-isopropenyl-5-methylcyclohexanol (isopulegol), 1-isopropyl-4-methylcyclohex-3-enol (terpinenol), 4-isopropylcyclohexanol, 1-(4-isopropylcyclohexyl) ethanol, 4-isopropylcyclohexylmethanol, 2-isopropyl-5-methylcyclohexanol (menthol), 2-isopropyl-5-methylphenol (thymol), 5-isopropyl-2-methylphenol (carvacrol), 2-(4-methyl-3-cyclohexenyl)-2-propanol (terpineol), 2-(4-methylcyclohexyl)-2-propanol (dihydroterpineol), 4-methoxybenzyl alcohol, 2-methoxy-4-methylphenol, 3-methoxy-5-methylphenol, 1-methoxy-4-propenylbenzene (anethol), 2-methoxy-4-propenylphenol (isoeugenol), 4-methyl-3-decen-5-ol, 2-methyl-6-methylene-7-octen-2-ol (myrcenol), 3-methyl-4-phenyl-2-butanol, 2-(2-methylphenyl) ethanol, 2-methyl-4-phenyl-1-pentanol, 3-methyl-5-phenyl-1-pentanol, 2-methyl-1-phenyl-2-propanol, (1-methyl-2-(1,2,2-trimethylbicyclo[3.1.0]hex-3-ylmethyl) cyclopropyl) methanol, 3-methyl-4-(2,2,6-trimethylcyclohexen-1-yl)-2-butanol, 2-methyl-4-(2,2,3-trimethyl-3-cyclopenten-1-yl)-2-buten-1-ol, (3-methyl-1-(2,2,3-trimethyl-3-cyclopentenyl)-3-cyclohexen-1-yl) methanol, 3-methyl-5-(2,2,3-trimethyl-3-cyclopenten-1-yl)-4-penten-2-ol, 2-methyl-2-vinyl-5-(1-hydroxy-1-methylethyl) tetrahydrofuran, trans,cis-2,6-nonadienol, 1-nonanol, nopol, 1,2,3,4,4a,5,6,7-octahydro-2,5,5-trimethyl-2-naphthol, 1-octanol, 3,4,5,6,6-pentamethyl-2-heptanol, 2-phenylethanol, 2-phenylpropanol, 3-phenylpropanol (hydrocinnamic alcohol), 3-phenyl-2-propen-1-ol (cinnamic alcohol), 4-(5,5,6-trimethylbicyclo[2.2.1]hept-2-yl) cyclohexan-1-ol, 3,5,5-trimethylcyclohexanol, 2,4,6-trimethyl-4-cyclohexen-1-ylmethanol, 5-(2,2,3-trimethyl-3-cyclopentenyl)-3-methylpentan-2-ol, 3,7,11-trimethyl-2,6,10-dodecatrien-1-ol (farnesol), 3,7,11-trimethyl-1,6,10-dodecatrien-3-ol (nerolidol), 3,5,5-trimethyl-1-hexanol (isononanol), 1-undecanol, 10-undecen-1-ol and vetiverol.

Anions A⁻ of physiologically compatible acids HA within the meaning of the invention are all anions having no caustic or markedly irritating effect on human skin. The anions A⁻ are preferably chosen from the series comprising chloride, bromide, methyl sulfate, ethyl sulfate, sulfate, nitrate, phosphate or hydrogen phosphate.

The organopolysiloxanes according to the invention can be obtained by reacting organopolysiloxanes containing a tertiary amino group with a chloroacetic acid ester of a fragrance alcohol. Chloroacetic acid esters of fragrance alcohols can be obtained by known means by reacting chloroacetic acid chloride with the fragrance alcohol, the reaction preferably being performed in the presence of a base which binds the hydrogen chloride released in the reaction.

Organopolysiloxanes containing a tertiary amino group are obtainable through a series of known methods. A general way of producing these compounds is the reaction of a secondary amine with an organopolysiloxane containing a suitable leaving group in a nucleophilic substitution reaction. A special embodiment of this reaction is the reaction of an organopolysiloxane containing a radical having an epoxide grouping with a secondary amine, with ring opening of the epoxide and formation of a beta-amino alcohol.

The preferred organopolysiloxanes, in which the betaine ester groups are coupled to silicon atoms of the organopolysiloxane via hydroxyethylene bridges, are preferably obtained by reacting an organopolysiloxane comprising at least one Si—H group with an ethanolamine having the structure $HO-CH_2-CH_2-NR^1R^2$, with subsequent reaction with a chloroacetic acid ester of a fragrance alcohol, wherein $R^1$ and $R^2$ have the previously cited meaning.

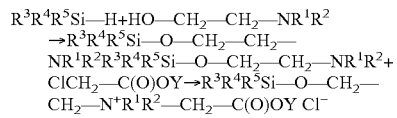
$$R^3R^4R^5Si-H + HO-CH_2-CH_2-NR^1R^2$$
$$\rightarrow R^3R^4R^5Si-O-CH_2-CH_2-$$
$$NR^1R^2 R^3R^4R^5Si-O-CH_2-CH_2-NR^1R^2 +$$
$$ClCH_2-C(O)OY \rightarrow R^3R^4R^5Si-O-CH_2-$$
$$CH_2-N^+R^1R^2-CH_2-C(O)OY\ Cl^-$$

In an aqueous dispersion the organopolysiloxanes according to the invention display a high resistance to hydrolysis and are capable of attaching to textile fibres, skin or hair from the aqueous dispersion. Within the meaning of the invention the term aqueous dispersion is not restricted to dispersions of solid organopolysiloxanes but also includes emulsions of liquid organopolysiloxanes as well as microemulsions and micellar solutions. The organopolysiloxanes according to the invention are therefore suitable as constituents of textile treatment agents or personal care products and can give such agents and products the property that textiles treated with the textile treatment agent or hair or skin areas treated with the personal care product display a long-lasting fragrance which derives from the delayed release of the fragrance alcohol from the organopolysiloxane.

Organopolysiloxanes according to the invention are preferred here which release the fragrance alcohol Y—OH in the aqueous dispersion more quickly at a pH of 3 than at a pH of 9. The faster release of the fragrance alcohol in the acid range is unexpected and was not foreseeable, since the betaine esters of fragrance alcohols known from the prior art all release the fragrance alcohol more slowly at a pH of 3 than at a pH of 9.

These preferred organopolysiloxanes can be used to provide textile treatment agents or personal care products, wherein textiles treated with the textile treatment agent or hair or skin areas treated with the personal care product develop a stronger fragrance through the release of the fragrance alcohol when they are wetted with sweat and the bacterial degradation of constituents of the sweat causes the pH to fall. Textile treatment agents or personal care products containing such organopolysiloxanes can thus effectively conceal the formation of unpleasant odours which arise through a bacterial degradation of constituents of the sweat.

The textile treatment agents according to the invention contain at least one organopolysiloxane according to the invention and are preferably intended for a treatment of textiles with an aqueous solution or dispersion of the textile treatment agent, from which the organopolysiloxanes according to the invention attach to the textile fibres. In addition to the targeted release of the fragrance alcohol, the organopolysiloxanes according to the invention also bring about a softer feel of the fabric to the fibres of which the organopolysiloxane is attached. The textile treatment agents according to the invention thus also display fabric softening properties.

The textile treatment agents according to the invention can be in solid form, for example in the form of powders, granules or mouldings, such as extrudates, pellets, briquettes or tablets. Textile treatment agents in solid form can also contain liquid organopolysiloxanes according to the invention which are applied to suitable support materials. Porous solid constituents of the textile treatment agent which fulfil an additional function in the textile treatment agent are preferably used as support materials for liquid organopolysiloxanes according to the invention. Textile treatment agents in the form of mouldings which are produced by press agglomeration methods, such as extrusion, briquetting or tabletting, can additionally contain binders to improve the strength of the mouldings. The textile treatment agents preferably contain no additional binders, however, and a functional component of the textile treatment agent, preferably a non-ionic surfactant, acts as a binder.

In alternative embodiments the textile treatment agents according to the invention can also be liquid or in the form of a gel. In these embodiments the textile treatment agent preferably contains the organopolysiloxane according to the invention in dissolved or dispersed form, wherein the term dispersed form covers both dispersions of solid organopolysiloxanes and emulsions of liquid organopolysiloxanes, as well as microemulsions and micellar solutions.

Textile treatment agents in liquid form can display isotropic, thixotropic, pseudoplastic or shear-thinning rheological properties. In order to adjust the rheological properties, liquid or gel-like textile treatment agents can contain as additives swelling clays, in particular montmorillonites, precipitated or pyrogenic silicas, vegetable gums, in particular xanthans, or polymeric gelling agents, such as vinyl polymers containing carboxyl groups. These additives firstly give the textile treatment agent the desired viscosity and secondly maintain insoluble constituents dispersed in the textile treatment agent in dispersed form.

Detergents containing at least one surfactant and at least one organopolysiloxane according to the invention are a preferred embodiment of the textile treatment agents according to the invention. Detergents within the meaning of the invention are all preparations which are suitable for cleaning textiles in an aqueous washing liquor.

Suitable surfactants for the detergents according to the invention are above all anionic, non-ionic and cationic surfactants.

Suitable anionic surfactants are, for example, surfactants having sulfonate groups, preferably alkyl benzene sulfonates, alkane sulfonates, alpha-olefin sulfonates, alpha-sulfo fatty acid esters or sulfosuccinates. Alkyl benzene sulfonates having a straight-chain or branched alkyl group with 8 to 20 carbon atoms, in particular with 10 to 16 carbon atoms, are preferred. Preferred alkane sulfonates are examples having straight-chain alkyl chains with 12 to 18 carbon atoms. As alpha-olefin sulfonates the reaction products from the sulfonation of alpha-olefins having 12 to 18 carbon atoms are preferably used. As alpha-sulfo fatty acid esters, sulfonation products of fatty acid esters produced from fatty acids having 12 to 18 carbon atoms and short-chain alcohols having 1 to 3 carbon atoms are preferred. Surfactants having a sulfate group in the molecule, preferably alkyl sulfates and ether sulfates, are also suitable as anionic surfactants. Preferred alkyl sulfates are examples having straight-chain alkyl radicals with 12 to 18 carbon atoms. Also suitable are beta-branched alkyl sulfates and alkyl sulfates which are monoalkyl- or polyalkyl-substituted in the middle of the longest alkyl chain. Preferred ether sulfates are the alkyl ether sulfates obtained by ethoxylation of linear alcohols having 12 to 18 carbon atoms with 2 to 6 ethylene oxide units and subsequent sulfation. Finally soaps can also be used as anionic surfactants, such as e.g. alkali metal salts of lauric acid, myristic acid, palmitic acid, stearic acid and/or natural fatty acid blends, such as e.g. coconut, palm kernel or tallow fatty acids.

Alkoxylated compounds, for example, are suitable as non-ionic surfactants, in particular ethoxylated and propoxylated compounds. Particularly suitable are condensation products of alkyl phenols or fatty alcohols with 1 to 50 mol, preferably 1 to 10 mol, of ethylene oxide and/or propylene oxide. Also suitable are polyhydroxy fatty acid amides, wherein an organic radical having one or more hydroxyl groups, which can also be alkoxylated, is bonded to the amide nitrogen. Also suitable as non-ionic surfactants are alkyl glycosides having a straight-chain or branched alkyl group with 8 to 22 carbon atoms, in particular with 12 to 18 carbon atoms, and a monoglycoside or diglycoside radical which is preferably derived from glucose.

Suitable cationic surfactants are, for example, monoalkoxylated and dialkoxylated quaternary amines having a $C_6$ to $C_{18}$ alkyl radical bonded to the nitrogen and one or two hydroxyalkyl groups.

In addition to at least one organopolysiloxane according to the invention and at least one surfactant, the detergents according to the invention can also contain as additional components builders, alkaline components, bleaching agents, bleach activators, enzymes, chelating complexing agents, greying inhibitors, foam inhibitors, optical brighteners, fragrances and dyes, for example.

The detergents according to the invention can contain builders which are able to bind dissolved calcium and magnesium ions when used in water. Suitable builders are alkali metal phosphates and alkali metal polyphosphates, in particular pentasodium triphosphate; water-soluble and water-insoluble sodium silicates, in particular layered silicates having the formula $Na_5Si_2O_5$; zeolites having the structures A, X and/or P; and trisodium citrate. In addition to the builders, organic co-builders can also be used, such as e.g. polyacrylic acid, polyaspartic acid and/or acrylic acid copolymers with methacrylic acid, acrolein or sulfonic acid-containing vinyl monomers, and the alkali metal salts thereof.

The detergents according to the invention also generally contain alkaline components which when used in accordance with requirements bring about a pH in the range from 8 to 12 in the washing liquor or the aqueous detergent solution. Sodium carbonate, sodium sesquicarbonate, sodium metasilicate and other soluble alkali metal silicates are suitable above all as alkaline components.

The detergents according to the invention can also contain bleaching agents, such as e.g. alkali metal perborates, alkali metal carbonate perhydrates, alkali metal persilicates, alkali metal persulfates, alkali metal peroxophosphates, alkali metal peroxopyrophosphates, diacyl peroxides, aromatic peroxy acids and aliphatic peroxy acids. Preferred bleaching agents are sodium perborate tetrahydrate, sodium perborate monohydrate, sodium carbonate perhydrate, peroxy lauric acid, peroxy stearic acid, epsilon-phthalimido-peroxycarboxylic acid, 1,12-diperoxydodecanedioic acid, 1,9-diperoxyazelaic acid and 2-decyldiperoxybutane-1,4-dioic acid. Particularly preferred are sodium perborate tetrahydrate, sodium perborate monohydrate and sodium carbonate perhydrate, in particular sodium carbonate perhydrate. A suitable sodium carbonate perhydrate for use in liquid detergents is known from WO 2004/056955.

In addition to bleaching agents the detergents according to the invention can also contain bleach activators. Compounds having one or more acyl groups bonded to nitrogen or oxygen and capable of perhydrolysis, which react in the washing liquor with hydrogen peroxide released from a bleaching agent to form peroxycarboxylic acids, are suitable above all as bleach activators for the detergents according to the invention. Examples of such compounds are polyacylated alkylene diamines, such as in particular tetraacetyl ethylene diamine (TAED); acylated triazine derivatives, in particular 1,5-diacetyl-2,4-dioxohexahydro-1,3,5-triazine (DADHT); acylated glycolurils, in particular tetraacetyl glycoluril (TAGU); N-acylimides, in particular N-nonanoyl succinimide (NOSI); acylated phenol sulfonates, in particular n-nonanoyl or iso-nonanoyl oxybenzene sulfonate (n- or iso-NOBS); carboxylic anhydrides, such as phthalic anhydride; acylated polyhydric alcohols, such as ethylene glycol diacetate, 2,5-diacetoxy-2,5-dihydrofuran, acetylated sorbitol and mannitol and acylated sugars, such as pentaacetyl glucose; enol esters; and N-acylated lactams, in particular N-acyl caprolactams and N-acyl valerolactams. Also suitable as bleach activators are amino-functionalised nitriles and salts thereof (nitrile quats), which are known for example from the journal Tenside Surf. Det. 1997, 34(6), pages 404–409. Transition metal complexes, which can activate hydrogen peroxide for stain removal by bleaching, can also be used as bleach activators. Suitable transition metal complexes are known for example from EP-A 0 544 490 page 2, line 4 to page 3, line 57; WO 00/52124 page 5, line 9 to page 8, line 7 and page 8, line 19 to page 11, line 14; WO 04/039932, page 2, line 25 to page 10, line 21; WO 00/12808 page 6, line 29 to page 33, line 29; WO 00/60043 page 6, line 9 to page 17, line 22; WO 00/27975, page 2, lines 1 to 18 and page 3, line 7 to page 4, line 6; WO 01/05925, page 1, line 28 to page 3, line 14; WO 99/64156, page 2, line 25 to page 9, line 18; and GB-A 2 309 976, page 3, line 1 to page 8, line 32.

The detergents according to the invention can also contain enzymes, which intensify the cleaning action, in particular lipases, cutinases, amylases, neutral and alkaline proteases, esterases, cellulases, pectinases, lactases and/or peroxidases. The enzymes here can be adsorbed on support materials or encapsulated in coating substances to protect them against decomposition.

The detergents according to the invention can also contain chelating complexing agents for transition metals, which can be used to prevent a catalytic decomposition of active oxygen compounds in the washing liquor. Phosphonates, such as hydroxyethane-1,1-disphosphonate, nitrilotrimethylene phosphonate, diethylene triamine penta(methylene phosphonate), ethylene diamine tetra(methylene phosphonate), hexamethylene diamine tetra(methylene phosphonate) and the alkali metal salts thereof are suitable, for example. Also suitable are nitrilotriacetic acid and polyaminocarboxylic acids, such as in particular ethylene diamine tetraacetic acid, diethylene triamine pentaacetic acid, ethylene diamine-N,N'-disuccinic acid, methyl glycine diacetic acid and polyaspartates, as well as the alkali metal and ammonium salts thereof. Finally, polybasic carboxylic acids and in particular hydroxycarboxylic acids, such as in particular tartaric acid and citric acid, are also suitable as chelating complexing agents.

The detergents according to the invention can additionally contain greying inhibitors, which hold the dirt detached from the fibres in suspension and prevent the dirt from reattaching to the fibres. Suitable greying inhibitors are, for example, cellulose ethers, such as carboxymethyl cellulose and alkali metal salts thereof, methyl cellulose, hydroxyethyl cellulose and hydroxypropyl cellulose. Polyvinyl pyrrolidone is also suitable.

The detergents according to the invention can also contain foam inhibitors, which reduce foaming in the washing liquor. Suitable foam inhibitors are for example organopolysiloxanes such as polydimethyl siloxane, paraffins and/or waxes, and mixtures thereof with fine-particle silicas.

The detergents according to the invention can optionally contain optical brighteners, which attach to the fibres, absorb light in the UV range and fluoresce blue, to compensate for a yellowing of the fibres. Suitable optical brighteners are, for example, derivatives of diaminostilbene disulfonic acid, such as alkali metal salts of 4,4'-bis-(2-anilino-4-morpholino-1,3,5-triazinyl-6-amino)stilbene-2,2'-disulfonic acid or substituted diphenyl styryls, such as alkali metal salts of 4,4'-bis-(2-sulfostyryl) diphenyl.

The detergents according to the invention can finally also contain dyes, as well as further fragrances in addition to the organopolysiloxanes according to the invention.

Detergents according to the invention in liquid form or gel form can additionally also contain up to 30 wt. % of organic solvents, such as e.g. methanol, ethanol, n-propanol, isopropanol, n-butanol, ethylene glycol, 1,2-propylene glycol, 1,3-propylene glycol, 1,4-butylene glycol, glycerol, diethylene glycol, ethylene glycol methyl ether, ethanolamine, diethanolamine and/or triethanolamine.

The personal care products according to the invention contain at least one organopolysiloxane according to the invention and are intended for the care and/or cleansing of human skin and/or hair. Within the meaning of the invention the term personal care product includes inter alia soaps, liquid soaps, shower gels, cleansing and nourishing lotions, skin creams, shampoos, hair rinses and sunscreens.

The personal care products according to the invention can contain all constituents of personal care products known from the prior art, wherein the personal care product preferably contains no acidic components in non-neutralised form. In addition to at least one organopolysiloxane according to the invention, the personal care products according to the invention can also contain as additional components surfactants, emulsifiers, emollients, fats and waxes, pearlescent waxes, superfatting agents, film formers, hydrotropes, viscosity regulators, preservatives, moisturisers, silicones, antioxidants, UV light screening filters, anti-dandruff agents, deodorising actives, biogenic actives, dyes and perfume oils, for example.

The personal care products according to the invention can contain surfactants, especially if they are intended for cleansing skin and/or hair. Mild surfactants are preferably used here which have little irritating effect on the skin. Both anionic and non-ionic, cationic and/or amphoteric surfactants can be used.

Suitable anionic surfactants for the personal care products according to the invention are soaps, alkyl benzene sulfonates, alkane sulfonates, olefin sulfonates, alkyl ether sulfonates, glycerol ether sulfonates, alpha-methyl ester sulfonates, sulfo fatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acyl amino acids, such as e.g. acyl lactylates, acyl tartrates, acyl glutamates and acyl aspartates, alkyl oligoglucoside sulfates, protein fatty acid condensates (in particular wheat-based plant products) and alkyl (ether) phosphates.

Suitable non-ionic surfactants for the personal care products according to the invention are fatty alcohol polyglycol ethers, alkyl phenol polyglycol ethers, fatty acid polyglycol esters, fatty acid amide polyglycol ethers, fatty amine polyglycol ethers, alkoxylated triglycerides, partially oxidised alk(en)yl oligoglycosides or glucoronic acid derivatives, fatty acid N-alkyl glucamides, protein hydrolysates (in particular wheat-based plant products), polyol fatty acid esters, sugar esters, sorbitan esters, polysorbates and amine oxides.

Suitable cationic surfactants for the personal care products according to the invention are quaternary ammonium compounds, such as e.g. dimethyldistearyl ammonium chloride, imidazolinium quats and ester quats, in particular quaternised fatty acid trialkanol amine ester salts.

Suitable amphoteric surfactants for the personal care products according to the invention are alkyl betaines, alkyl amido betaines, amino propionates, amino glycinates and sulfobetaines.

Preferred mild surfactants for the personal care products according to the invention are fatty alcohol polyglycol ether sulfates, monoglyceride sulfates, monoalkyl sulfosuccinates, dialkyl sulfosuccinates, fatty acid isethionates, fatty acid sarcosinates, fatty acid taurides, fatty acid glutamates, alpha-olefin sulfonates, ether carboxylic acids, alkyl oligoglucosides, fatty acid glucamides, alkyl amido betaines, and protein fatty acid condensates.

The personal care products according to the invention can contain emulsifiers, with which stable emulsions of the O/W type or W/O type are obtained from water and water-insoluble constituents. The term emulsions here covers both liquid preparations and creamy and semisolid preparations. Both anionic and non-ionic, cationic and/or amphoteric emulsifiers can be used for the personal care products according to the invention.

Suitable anionic emulsifiers for the personal care products according to the invention are aliphatic fatty acids having 12 to 22 carbon atoms, such as e.g. palmitic acid, stearic acid or behenic acid, and dicarboxylic acids having 12 to 22 carbon atoms, such as e.g. azelaic acid or sebacic acid.

Suitable non-ionic emulsifiers for the personal care products according to the invention are alkoxylation products of linear fatty alcohols having 8 to 22 carbon atoms, fatty acids having 12 to 22 carbon atoms, alkyl phenols having 14 to 21 carbon atoms, alkylamines having 8 to 22 carbon atoms and of castor oil and/or hydrogenated castor oil, the alkoxylation products preferably containing 2 to 30 mol of ethylene oxide and/or 1 to 5 mol of propylene oxide. Also suitable are alkyl oligoglycosides having 8 to 18 carbon atoms in the alkyl radical; partial glycerides, such as hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride or malic acid diglyceride; sorbitan esters, such as sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate or sorbitan trimaleate; and the ethoxylation products of these compounds with 2 to 30 mol of ethylene oxide. Suitable non-ionic emulsifiers are also polyglycerol esters, such as polyglyceryl-2 dipolyhydroxystearate (Dehymuls PGPH), polyglycerol-3 diisostearate (Lameform TGI), polyglyceryl-4 isostearate (Isolan GI 34), polyglyceryl-3 oleate, diisostearoyl polyglyceryl-3 diisostearate (Isolan PDI), polyglyceryl-3 methylglucose distearate (Tego Care 450), polyglyceryl-3 beeswax (Cera bellina), polyglyceryl-4 caprate (polyglycerol caprate T2010/90), polyglyceryl-3 cetyl ether (Chimexane NL), polyglyceryl-3 distearate (Cremophor GS32) and polyglyceryl polyricinoleate (Admul WOL 1403).

Suitable cationic emulsifiers for the personal care products according to the invention are quaternised fatty acid alkanolamine esters, which are obtained by esterification of alkanolamines, preferably triethanolamine or methyl diethanolamine, with fatty acids and subsequent quaternisation with an alkylating agent, preferably dimethyl sulfate or ethylene oxide. Fatty acid blends of natural origin, which were preferably obtained from vegetable or animal oils or fats and contain predominantly C16 and C18 fatty acids, are preferably used as fatty acids, wherein the fatty acid blends can be used with the natural degree of unsaturation, partially hydrogenated or fully hydrogenated. Fatty acid blends having an iodine value in the range from 5 to 50 are preferably used. Quaternised fatty acid triethanolamine esters having an average degree of esterification in the range from 1.5 to 2.0 mol of fatty acid per mol of triethanolamine are particularly preferred.

Suitable amphoteric emulsifiers for the personal care products according to the invention are betaines, such as N-alkyl-N,N-dimethylammonium glycinates, N-acylaminopropyl-N,N-dimethylammonium glycinates and 2-alkyl-3-carboxymethyl-3-hydroxyethyl imidazolines, each having 8 to 18 carbon atoms in the alkyl or acyl group, preferably the compound known under the CTFA name cocoamidopropyl betaine. Also suitable are N-alkyl glycines, N-alkyl propionic acids, N-alkyl aminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids, each having about 8 to 18 carbon atoms in the alkyl group.

The personal care products according to the invention can contain emollients, which can dissolve water-insoluble active ingredients and determine the sensorial properties of the personal care products alone or in combination with emulsifiers. Within the meaning of the invention emollients are substances or mixtures of substances which are liquid at 20° C. and are immiscible with water at 25° C.

Suitable emollients are guerbet alcohols based on fatty alcohols having 6 to 18, preferably 8 to 10 carbon atoms (for example Eutanol G), esters of linear $C_6$–$C_{22}$ fatty acids with linear or branched $C_6$–$C_{22}$ fatty alcohols and esters of branched $C_6$–$C_{13}$ carboxylic acids with linear or branched $C_6$–$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate; esters of $C_3$–$C_{38}$ alkyl hydroxycarboxylic acids with linear or branched $C_6$–$C_{22}$ fatty alcohols, for example diethylhexyl malate; and esters of linear or branched fatty acids with polyhydric alcohols, such as propylene glycol, dipropylene glycol or tripropylene glycol, for example. Also suitable are triglycerides based on $C_6$–$C_{10}$ fatty acids; liquid mono-, di- and triglyceride blends based on $C_6$–$C_{18}$ fatty acids; esters of $C_6$–$C_{22}$ fatty alcohols or guerbet alcohols with aromatic carboxylic acids, such as benzoic acid; esters of $C_2$–$C_{12}$ dicarboxylic acids with linear or branched alcohols having 1 to 22 carbon atoms or polyols having 2 to 10 carbon atoms and 2 to 6 hydroxyl groups; vegetable oils; branched primary alcohols; linear and branched $C_6$–$C_{22}$ fatty alcohol carbonates, such as e.g. dicaprylyl carbonate (Cetiol CC); guerbet carbonates based on fatty alcohols having 6 to 18, preferably 8 to 10 carbon atoms; esters of benzoic acid with linear or branched $C_6$–$C_{22}$ alcohols, for example Finsolv TN; linear or branched, symmetrical or asymmetrical dialkyl ethers having 6 to 22 carbon atoms per alkyl group, such as e.g. dicaprylyl ether (Cetiol OE); ring-opening products of epoxidised fatty acid esters with polyols, for example Hydagen HSP, Sovermol 750, Sovermol 1102; and aliphatic hydrocarbons, such as e.g. mineral oil, vaseline, petroleum jelly, squalane, squalene or dialkyl cyclohexanes.

The personal care products according to the invention can contain fats and waxes, with which the sensorial properties of creamy and semisolid personal care products in particular can be adjusted. Suitable waxes are natural waxes, such as e.g. candelilla wax, carnauba wax, Japan wax, esparto grass wax, cork wax, guaruma wax, rice germ oil wax, sugar cane wax, ouricury wax, montan wax, beeswax, shellac wax, spermaceti wax, lanolin (wool wax), uropygial fat, ceresine, ozocerite (earth wax), petroleum jelly and paraffin waxes; chemically modified, hydrogenated waxes, such as e.g. montan ester waxes, sasol waxes and hydrogenated jojoba waxes; and synthetic waxes, such as e.g. polyalkylene waxes and polyethylene glycol waxes. Animal and vegetable fats, which substantially consist of mixed glycerol esters of higher fatty acids, are suitable as fats. Phospholipids, phosphatidylcholines, sphingosines and sphingolipids can also be used in place of fats.

The personal care products according to the invention can also contain pearlescent waxes, which give the personal care product an attractive appearance with a pearly gloss. Suitable pearlescent waxes are alkylene glycol esters, such as ethylene glycol distearate; fatty acid alkanolamides, such as coconut fatty acid diethanolamide; partial glycerides, such as stearic acid monoglyceride; esters of polybasic carboxylic acids, which can be substituted with hydroxyl groups, with fatty alcohols having 6 to 22 carbon atoms, in particular long-chain esters of tartaric acid; fatty alcohols, fatty alcohol ethers and fatty alcohol carbonates, which in total comprise at least 24 carbon atoms, such as distearyl ethers; fatty acids, such as stearic acid, hydroxystearic acid or behenic acid; ring-opening products of olefin oxides having 12 to 22 carbon atoms with fatty alcohols having 12 to 22 carbon atoms or polyols having 2 to 15 carbon atoms and 2 to 10 hydroxyl groups.

The personal care products according to the invention can also contain superfatting agents, such as lanolin or lecithin or ethoxylates of these compounds, polyol fatty acid esters, monoglycerides or fatty acid alkanolamides.

The personal care products according to the invention can also contain film formers, with which active ingredients can be fixed to the skin or hair. Suitable film formers are chitosan, microcrystalline chitosan, quaternised chitosan, polyvinyl pyrrolidone, vinyl pyrrolidone-vinyl acetate copolymers, polymers based on acrylic acid and methacrylic acid, quaternised celluloses, collagen, hyaluronic acid and salts thereof.

The personal care products according to the invention can also contain hydrotropes, such as ethanol, isopropanol or polyols, to improve the flow properties. Polyols having 2 to 15 carbon atoms and at least two hydroxyl groups, which can optionally contain other functional groups, in particular amino groups, are particularly suitable. Examples of such polyols are glycerol; alkylene glycols, such as ethylene glycol, diethylene glycol, propylene glycol, butylene glycol, pentylene glycol, hexylene glycol, and polyethylene glycols having an average molecular weight of 100 to 1000 g/mol; oligoglycerol blends with a degree of condensation of 1.5 to 10, such as technical diglycerol blends having a diglycerol content of 40 to 50 wt. %; methylol compounds, such as trimethylol ethane, trimethylol propane, trimethylol butane, pentaerythritol and dipentaerythritol; short-chain alkyl glucosides having 1 to 8 carbon atoms in the alkyl radical, such as methyl and butyl glucosides; sugar alcohols having 5 to 12 carbon atoms, such as sorbitol or mannitol; sugars having 5 to 12 carbon atoms, such as glucose or sucrose; amino sugars such as glucamine; and dialkanolamines, such as diethanolamine or 2-amino-1,3-propanediol.

The personal care products according to the invention can additionally contain viscosity regulators to improve the viscosity of the product and optionally to thicken the product. Suitable viscosity regulators are natural hydrogel formers, such as xanthan gum, guar, agar-agar, alginates and tyloses; modified polysaccharides, such as cellulose ethers and cellulose esters, for example carboxymethyl cellulose, methyl cellulose, hydroxyethyl cellulose, methylhydroxyethyl cellulose and methylhydroxypropyl cellulose; inorganic hydrocolloids, such as bentonites, magnesium-aluminium silicates and silicon dioxide; synthetic hydrocolloids, such as polyacrylates (commercially obtainable as Carbopols and Pemulen grades from Goodrich, Synthalens from Sigma, Keltrol grades from Kelco, Sepigel grades from Seppic and Salcare grades from Allied Colloids), uncrosslinked and polyol-crosslinked polyacrylic acids, polyacrylamides, polyvinyl alcohols and polyvinyl pyrrolidones; electrolytes, such as common salt and ammonium chloride; and anionic, zwitterionic, amphoteric and non-ionic copolymers, such as vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and esters thereof, acrylamidopropyl trimethylammonium chloride/acrylate copolymers, octyl acrylamide/methyl methacrylate/tert-butyl aminoethyl methacrylate/2-hydroxypropyl methacrylate copolymers, vinyl pyrrolidone/vinyl acetate copolymers and vinyl pyrrolidone/dimethyl aminoethyl methacrylate/vinyl caprolactam terpolymers. Other suitable thickeners are listed in Cosm. Toil. 108, 95 (1993).

The personal care products according to the invention can also contain preservatives, which prevent constituents of the personal care product from being broken down by bacteria during storage. Suitable preservatives are phenoxyethanol, formaldehyde solution, parabens, pentanediol or sorbic acid and the silver complexes known under the name Surfacine™. Other suitable preservatives are known from Annex 6, Part A and B of the German cosmetics ordinance.

The personal care products according to the invention can additionally contain moisturisers, which regulate the moisture of the treated skin and can additionally improve the sensorial properties of the personal care product. Suitable moisturisers are natural amino acids, pyrrolidone carboxylic acid, lactic acid and salts thereof, lactitol, urea and urea derivatives, uric acid, glucosamine, creatinine, cleavage products of collagen, chitosan or chitosan salts/derivatives. Also suitable are polyols and polyol derivatives, such as glycerol, diglycerol, triglycerol, ethylene glycol, propylene glycol, butylene glycol, pentylene glycol, erythritol and 1,2,6-hexanetriol; polyethylene glycols, such as PEG-4, PEG-6, PEG-7, PEG-8, PEG-9, PEG-10, PEG-12, PEG-14, PEG-16, PEG-18 and PEG-20; sugars and sugar derivatives, such as fructose, glucose, maltose, maltitol, mannitol, inositol, sorbitol, sucrose, trehalose, xylose, xylitol and glucuronic acid and salts thereof; and ethoxylated sorbitol, such as Sorbeth-6, Sorbeth-20, Sorbeth-30 and Sorbeth-40. Also suitable are honey and hydrogenated honey, hydrogenated starch hydrolysates and mixtures of hydrogenated wheat protein and PEG-20 acetate copolymer. Glycerol, diglycerol, triglycerol or butylene glycol are preferably used as moisturisers.

The personal care products according to the invention can also contain silicones having the structural type of cyclomethicones, dimethicones, dimethylpolysiloxanes, methylphenylpolysiloxanes, cyclic silicones, and amino-, fatty acid-, alcohol-, polyether-, epoxy-, fluorine-, glycoside- and alkyl-modified silicone compounds. Also suitable are simethicones, which are mixtures of dimethicones having an average chain length of 200 to 300 dimethyl siloxane units and silicon dioxide or hydrogenated silicates.

The personal care products according to the invention can additionally contain antioxidants, which can interrupt the photochemical reaction chain which is triggered when UV radiation penetrates into the skin. Suitable antioxidants are amino acids, such as glycine, histidine, tyrosine and tryptophane and derivatives thereof; peptides, such as D,L-carnosine, D-carnosine and L-carnosine and derivatives thereof, such as anserine for example; carotenoids and carotenes, such as alpha-carotene, beta-carotene and lycopine and derivatives thereof; chlorogenic acid and derivatives thereof; lipoic acid and derivatives thereof, such as dihydrolipoic acid; aurothioglucose, propyl thiouracil and other thiols, such as thioredoxin, glutathione, cysteine, cystine and cystamine and their glycosyl, N-acetyl, methyl, ethyl, propyl, amyl, butyl, lauryl, palmitoyl, oleyl, gamma-linoleyl, cholesteryl and glyceryl esters, and salts thereof; dilauryl thiodipropionate, distearyl thiodipropionate and thiodipropionic acid and their esters, ethers, peptides, lipids, nucleotides, nucleosides and salts; sulfoximine compounds, such as buthionine sulfoximines, homocysteine sulfoximine, buthionine sulfones and penta-, hexa- and heptathionine sulfoximine; metal chelating compounds, such as alpha-hydroxy fatty acids, palmitic acid, phytic acid, lactoferrin, alpha-hydroxy acids, in particular citric acid, lactic acid and malic acid, humic acid, bile acid, bile extracts, bilirubin, biliverdin, EDTA and EGTA; unsaturated fatty acids and derivatives thereof, such as gamma-linolenic acid, linoleic acid and oleic acid; folic acid and derivatives thereof; ubiquinone and ubiquinol and derivatives thereof; vitamin C and derivatives thereof, such as ascorbyl palmitate, Mg-ascorbyl phosphate and ascorbyl acetate; tocopherols and derivatives thereof, such as vitamin E acetate; and vitamin A and derivatives thereof, such as vitamin A palmitate. Also suitable as antioxidants are rutic acid and derivatives thereof, such as alpha-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof, such as zinc oxide, selenium and derivatives thereof, such as selenomethionine, and stilbenes and derivatives thereof, such as stilbene oxide.

The personal care products according to the invention can also contain UV light screening filters, which absorb UV-A radiation and/or UV-B radiation. Both organic substances and inorganic pigments can be used as UV light screening filters, wherein the organic substances can be both oil-soluble or water-soluble and insoluble. Suitable oil-soluble UV-B light screening filters are 3-benzylidene camphor and 3-benzylidene norcamphor and derivatives thereof, such as 3-(4-methylbenzylidene) camphor, known from EP-A 0 693 471; 4-aminobenzoic acid derivatives, preferably 4-(dim ethylamino)benzoic acid-2-ethylhexyl ester, 4-(dimethylamino)benzoic acid-2-octyl ester and 4-(dimethylamino) benzoic acid amyl ester; esters of cinnamic acid, preferably 4-methoxycinnamic acid-2-ethylhexyl ester, 4-methoxycinnamic acid propyl ester, 4-methoxycinnamic acid isoamyl ester, and 2-cyano-3,3-phenylcinnamic acid-2-ethylhexyl ester (Octocrylene); esters of salicylic acid, preferably salicylic acid-2-ethylhexyl ester, salicylic acid-4-isopropylbenzyl ester and salicylic acid homomenthyl ester; derivatives of benzophenone, preferably 2-hydroxy-4-methoxybenzophenone, 2-hydroxy-4-methoxy-4'-methylbenzophenone and 2,2'-dihydroxy-4-methoxybenzophenone; esters of benzalmalonic acid, preferably 4-methoxybenzalmalonic acid di-2-ethylhexyl ester; triazine derivatives, such as 2,4,6-trianilino-(p-carbo-2'-ethyl-1'-hexyloxy)-1,3,5-triazine, octyl triazone, known from EP-A 0 818 450 and dioctyl butamidotriazone (Uvasorb HEB); propane-1,3-diones, such as 1-(4-tert-butylphenyl)-3-(4'-methoxyphenyl) propane-1,3-dione; and ketotricyclo(5.2.1.0)decane derivatives, known from EP-A 0 694 521. Suitable water-soluble UV-B light screening filters are 2-phenylbenzimidazole-5-sulfonic acid and the alkali, alkaline-earth, ammonium, alkylammonium, alkanolammonium and glucammonium salts thereof; sulfonic acid derivatives of benzophenones, preferably 2-hydroxy-4-methoxybenzophenone-5-sulfonic acid and salts thereof; and sulfonic acid derivatives of 3-benzylidene camphor, such as 4-(2-oxo-3-bornylidene methyl) benzene sulfonic acid and 2-methyl-5-(2-oxo-3-bornylidene) sulfonic acid and salts thereof. Suitable as organic UV-A light screening filters are derivatives of benzoyl methane, such as 1-(4'-tert-butyl phenyl)-3-(4'-methoxyphenyl) propane-1,3-dione, 4-tert-butyl-4'-methoxydibenzoylmethane (Parsol 1789) and 1-phenyl-3-(4'-isopropylphenyl) propane-1,3-dione, and the enamine compounds known from DE 191 12 033. The UV-A and UV-B light screening filters can naturally also be used in mixtures. Preferred combinations consist of derivatives of benzoyl methane, such as 4-tert-butyl-4'-methoxydibenzoyl methane and 2-cyano-3,3-phenyl cinnamic acid-2-ethylhexyl ester in combination with esters of cinnamic acid, such as 4-methoxycinnamic acid-2-ethylhexyl ester, 4-methoxycinnamic acid propyl ester or 4-methoxycinnamic acid isoamyl ester. Such combinations are advantageously combined with water-soluble filters, such as 2-phenyl benzimidazole-5-sulfonic acid and the alkali, alkaline-earth, ammonium, alkylammonium, alkanolammonium and glucammonium salts thereof. Suitable inorganic light screening pigments are finely dispersed metal oxide powders, which are preferably in hydrophobised form, in particular titanium dioxide powders, aluminium oxide powders, zinc oxide powders and mixed oxide powders with the elements Si, Ti, Al, Zn, Fe, B, Zr and/or Ce. So-called micropigments or nanopigments are preferably used, whose particles have an average diameter of less than 100 nm, preferably between 5 and 50 nm and in particular between 15 and 30 nm. They can have a spherical form, but such particles having an ellipsoid form or other form deviating from the spherical shape can also be used. Examples of commercial inorganic light stabilising pigments are coated titanium dioxides UV-titanium M212, M 262 and X 111 from Kemira, AEROXIDE $TiO_2$ P25, PF2, T 805 and T 817 from Degussa, micro titanium dioxide MT-150 W, MT-100 AQ, MT-100 SA, MT-100 HD and MT-100 TV from Tayca, Eusolex T2000 from Merck, zinc oxide neutral H&R and zinc oxide NDM from Haarmann & Reimer and Z-Cote and Z-Cote HP1 from BASF. Other suitable UV light screening filters are known from the review by P. Finkel in SÖFW-Journal 122, 543 (1996) and Parf. Kosm. 3, 11 (1999).

Personal care products according to the invention for the treatment of hair can also contain anti-dandruff agents. Suitable anti-dandruff agents are 1-hydroxy-4-methyl-6-(2,4,4-trimethylpentyl)-2-(1H)-pyridinone monoethanolamine, climbazole, ketoconazole, elubiol, selenium disulfide, colloidal sulfur, sulfur polyethylene glycol sorbitan monooleate, sulfur ricinol polyethoxylate, sulfur tar distillates, salicylic acid in combination with hexachlorophene, undecylenic acid monoethanolamide sulfosuccinate sodium, protein undecylenic acid condensates, zinc pyrithione, aluminium pyrithione and magnesium pyrithione.

The personal care products according to the invention can additionally contain deodorising actives. Suitable deodorising actives are astringent metal salts which have an antiperspirant action, germ-inhibiting agents, enzyme inhibitors and odour absorbers, which can be used alone or in combination. Suitable astringent metal salts having an antiperspirant action are aluminium chlorohydrates, aluminium zirconium chlorohydrates, aluminium hydroxylactates and zinc salts. Suitable commercial products are Locron from Clariant and Rezal 36G from Reheis. All substances which are active against gram-positive bacteria are suitable in principle as germ-inhibiting agents, such as e.g. 4-hydroxybenzoic acid and its salts and esters, N-(4-chlorophenyl)-N'-(3,4-dichlorophenyl) urea, 2,4,4'-trichloro-2'-hydroxydiphenyl ether (triclosan), 4-chloro-3,5-dimethylphenol, 2,2'-methylene bis-(6-bromo-4-chlorophenol), 3-methyl-4-(1-methylethyl) phenol, 2-benzyl-4-chlorophenol, 3-(4-chlorophenoxy)-1,2-propanediol, 3-iodo-2-propinyl butyl carbamate, chlorohexidine, 3,4,4'-trichlorocarbanilide (TTC), thymol, thyme oil, eugenol, clove oil, menthol, mint oil, farnesol, phenoxyethanol, glycerol monocaprinate, glycerol monocaprylate, glycerol monolaurate (GML), diglycerol monocaprinate (DMC), and salicylic acid-N-alkylamides, such as salicylic acid-n-octylamide or salicylic acid-n-decylamide. Suitable enzyme inhibitors are esterase inhibitors, preferably trialkyl citrates, such as trimethyl citrate, tripropyl citrate, triisopropyl citrate, tributyl citrate and in particular triethyl citrate; sterol sulfates and sterol phosphates, such as lanosterol, cholesterol, campesterol, stigmasterol and sitosterol sulfate or phosphate; dicarboxylic acids and esters thereof, such as glutaric acid, glutaric acid monoethyl ester, glutaric acid diethyl ester, adipic acid, adipic acid monoethyl ester, adipic acid diethyl ester, malonic acid and malonic acid diethyl ester; and hydroxycarboxylic acids and esters thereof such as e.g. citric acid, malic acid, tartaric acid or tartaric acid diethyl ester. Substances which can absorb and largely retain odour-producing compounds by reducing the partial pressure of the individual components are suitable as odour absorbers. As their main component, for example, they contain a complex zinc salt of ricinoleic acid or special, largely odour-neutral fragrances, which are known to the person skilled in the art as "fixatives", such as extracts of labdanum, styrax or certain abietic acid derivatives.

The personal care products according to the invention can also contain biogenicactives, such as tocopherol, tocopherol acetate, tocopherol palmitate, ascorbic acid, (deoxy)ribonucleic acid and fragmentation products thereof, beta-glucane, retinol, bisabolol, allantoin, phytantriol, panthenol, panthotenic acid, fruit acids, alpha-hydroxy acids, amino acids, ceramides, pseudoceramides, essential oils and vitamin complexes. Plant extracts, above all extracts of arnica, birch, camomile, burdock root, beard lichen, poplar, stinging nettle, prunus species, bambara nut and walnut shells, can also be used as biogenicactives.

The personal care products according to the invention can also contain dyes, both soluble dyes and insoluble pigments being suitable. Suitable soluble dyes are plant and animal dyes, such as betanin, bixin, carmine, carotene, chlorophyll or sepia, and synthetic organic dyes, such as azo, anthraquinone or triphenylmethane dyes, which are preferably water-soluble or dispersible in water. Suitable insoluble pigments are natural inorganic pigments, such as ochre, umber, red bole, sienna or chalk, and synthetic inorganic pigments such as iron oxides, ultramarines, titanium dioxide, zinc oxide or mica-based pigments, in particular pearlescent pigments.

Finally, the personal care products according to the invention can also contain perfume oils, to give the personal care product an attractive scent. The perfume oils used are conventionally mixtures of fragrance substances, wherein both natural and synthetic fragrance substances can be used. Suitable natural fragrance substances are extracts of flowers, stems and leaves, fruits, fruit skins, roots, woods, herbs and grasses, needles and twigs as well as resins and balsams. Suitable animal fragrance substances are civet and castoreum, for example. Typical synthetic fragrance substance compounds are products of the ester, ether, aldehyde, ketone, alcohol or hydrocarbon type. Fragrance substance compounds of the ester type are for example benzyl acetate, p-tert-butyl cyclohexyl acetate, linalyl acetate, phenylethyl acetate, linalyl benzoate, benzyl formate, allyl cyclohexyl propionate, styrallyl propionate and benzyl salicylate. The ethers include e.g. benzyl ethyl ethers, the aldehydes include e.g. the linear alkanals having 8 to 18 carbon atoms, citral, citronellal, citronellyloxy acetaldehyde, cyclamen aldehyde, hydroxy citronellal, lilial and bourgeonal, the ketones include e.g. the ionones and methyl cedryl ketone, the alcohols include anethol, citronellol, eugenol, isoeugenol, geraniol, linalool, phenylethanol and terpineol, the hydrocarbons primarily include the terpenes and balsams. Mixtures of various fragrance substances are preferably used, which together produce an attractive perfume note. Essential oils of relatively low volatility, which are mainly used as aroma components, are also suitable as perfume oils, for example sage oil, camomile oil, clove oil, melissa oil, mint oil, cinnamon leaf oil, lime-blossom oil, juniper berry oil, vetiver oil, olibanum oil, galbanum oil, labdanum oil and lavandin oil. Bergamot oil, dihydromyrcenol, lilial, lyral, citronellol, phenyl ethanol, alpha-hexylcinnamaldehyde, geraniol, benzyl acetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, beta-damascone, geranium oil bourbon, cyclohexyl salicylate, Vertofix Coeur, Iso-E-Super, Fixolide NP, evernyl, iraldein gamma, phenyl acetic acid, geranyl acetate, benzyl acetate, rose oxide, romilat, irotyl and floramat are preferably used, alone or in mixtures.

A further preferred embodiment of the textile treatment agents according to the invention are fragranced fabric rinses. Fragranced fabric rinses within the meaning of the invention are liquid preparations which contain an organopolysiloxane according to the invention in the form of an aqueous dispersion and from which the organopolysiloxane according to the invention attaches to textile fibres during the cleaning of textiles in an aqueous washing liquor when the fragranced fabric rinse is added to the water used for rinsing in a rinsing step, which is performed after the actual washing step.

Fragranced fabric rinses containing an organopolysiloxane according to the invention in liquid form preferably also contain at least one emulsifier, which forms a stable O/W emulsion with the liquid organopolysiloxane. The anionic, non-ionic and amphoteric emulsifiers previously cited as possible constituents of personal care products according to the invention are suitable as emulsifiers for the fragranced fabric rinses according to the invention.

The fragranced fabric rinses according to the invention preferably also contain buffering constituents with which the pH of the fragranced fabric rinse is held in the range from pH 5 to 9, preferably pH 6 to 8.

The fragranced fabric rinses according to the invention can moreover contain other components such as hydrotropes, viscosity regulators, preservatives, silicones and perfume oils, wherein the compounds previously cited as possible constituents of personal care products according to the invention are suitable. Furthermore, the fragranced fabric rinses according to the invention can also contain greying inhibitors, foam inhibitors, optical brighteners and dyes, which are suitable for the detergents according to the invention which have previously been described.

EXAMPLES

Example 1

Preparation of Chloroacetic Acid Citronellyl Ester

A mixture of 94.5 g (1.0 mol) of monochloroacetic acid and 203.2 g (1.4 mol) of 3,7-dimethyl-6-octen-1-ol (citronellol) was heated for 6 h at 50 mbar to 130° C., wherein the water formed by esterification was distilled off via a column. The reaction mixture obtained had an acid value of 5 mg KOH/g. Unreacted citronellol was then distilled off at 6 mbar and a bottoms temperature of up to 130° C. Distillation of the residue at 6 mbar yielded 198 g of chloroacetic acid citronellyl ester as a colourless liquid.

Example 2

Preparation of an Organopolysiloxane Having the Structure: $R^6$—O—[Si(CH$_3$)$_2$—O]$_n$—$R^6$, where n=10, $R^6$=—CH$_2$—CH$_2$—N$^+$(CH$_3$)$_2$—CH$_2$—C(O) OY Cl$^-$ and YOH=Citronellol A mixture of 346 g (0.4 mol) of alpha, omega-bis-(2-dimethylaminoethoxy)poly(dimethylsiloxane) having an average molecular weight of 865 g/mol and 163 g (0.7 mol) of chloroacetic acid citronellyl ester was heated for 11 h to 60° C. The product obtained had a content of free chloride of 4.43 wt. % and a content of organically bonded chloride of 0.05 wt. %, giving a conversion to betaine ester of 99%.

Example 3

Preparation of an Organopolysiloxane Having the Structure $R^6$—O—[Si(CH$_3$)$_2$—O]$_n$—$R^6$, where n=50, $R^6$=—CH$_2$—CH$_2$—N$^+$(CH$_3$)$_2$—CH$_2$—C(O) OY Cl$^-$ and YOH=Citronellol A mixture of 308.5 g (0.08 mol) of alpha, omega-bis-(2-dimethylaminoethoxy)poly(dimethylsiloxane) having an average molecular weight of 3856 g/mol and 32.6 g (0.14 mol) of chloroacetic acid citronellyl ester was heated for 56 h to 60° C. The product obtained had a content of free chloride of 2.29 wt. % and a content of organically bonded chloride of 0.04 wt. %, giving a conversion to betaine ester of 98%.

Example 4 pH-dependence of the Release of Citronellol from Aqueous Dispersions of the Organopolysiloxane from Example 3

The release of citronellol from the organopolysiloxane was determined at room temperature in commercial buffer solutions having pH values of 3, 6 and 9. 0.5 g of organopolysiloxane from example 3 and 0.5 g of emulsifier Rewopal C6 (cocomonoethanolamido polyglycol ether) were topped up with buffer solution to 50 ml, emulsified in an ultrasonic bath for 1 min and the stable emulsions that were formed were stored at room temperature. After the specified times, samples were taken, extracted with toluene and the proportion of released citronellol was determined with gas chromatography. Table 1 shows the amounts of released citronellol as a function of the time and the pH of the buffer solution, the numbers in each case being averages from two experiments.

The measurement results show that approximately 9% of the citronellol was released by ultrasonic dispersion. Thereafter at pH 6 and pH 9 the amount of citronellol released over 24 hours increased by only a further about 2%, in other words the betaine ester was stable. At pH 3, in contrast, a further about 42% of the citronellol was released over 24 hours.

TABLE 1

Amount of citronellol released

| Storage period in h | pH 3 | pH 6 | pH 9 |
|---|---|---|---|
| 0.25 | 10.3 | 9.4 | 8.8 |
| 2 |  | 9.8 | 8.7 |
| 2.5 | 17.3 |  |  |
| 24 | 52.0 | 11.1 | 10.8 |
| 36 | 62.0 |  | 11.4 |

Example 5

Use of the Organopolysiloxane from Example 3 in a Fragranced Fabric Rinse, Attachment of the Organopolysiloxane to Textile Fibres and Release of Citronellol Through the Action of Acid 20 g of the organopolysiloxane from example 3 and 5.0 g of Rewopal LA6 (lauryl alcohol ethoxylate with 6 EO units) were emulsified by stirring with 75 g of buffer solution having a pH of 7. 100 g of a fragranced fabric rinse emulsion were obtained.

In a domestic washing machine, 3.5 kg of cotton t-shirts were washed with WFT basic detergent, unperfumed, at 40° C. The fragranced fabric rinse emulsion was added to the final rinse cycle through the detergent drawer of the washing machine. The washed t-shirts were spun and dried on a line in air for at least 4 days until a fragrance could no longer be detected. When the t-shirts were subsequently sprayed with a 1 wt. % citric acid solution, a pronounced citronellol fragrance developed. Even after storing the t-shirts in a dry place for four weeks, a pronounced citronellol fragrance was still determined after spraying with the citric acid solution.

Example 6

Use of the Organopolysiloxane from Example 3 in a Fragranced Fabric Rinse, Softening Action of the Organopolysiloxane on Textile Fibres 3 kg of Frottana cotton towels measuring 80×50 cm and weighing 350 g/m² were washed twice with 75 g of IEC-A Base detergent from WKF-Testgewebe and twice without detergent in a Miele Mondia 1120 automatic washing machine at 95° C. and spun at 1200 min⁻¹. The washed pieces of fabric were dried on a line in air. 10 g of a fragranced fabric rinse emulsion produced as in example 5 were diluted to 2 l with tap water whilst being stirred. A piece of the washed test fabric was folded once and placed in a 40×50 cm tub and the diluted fragranced fabric rinse emulsion was poured over it. The fabric was kept in the tub for 10 min, during which time it was turned once, then spun for 2 min at 1200 min⁻¹ and dried on a line in air. The softness of the treated towel was then assessed sensorially by a panel of 9 testers, points from 0 (hard) to 5 (very soft) being allocated. For comparative purposes, a towel was assessed which had been treated with a fragranced fabric rinse emulsion, for the production of which a quaternary polysiloxane displaying the structure of the compound having formula (III) from EP-A 1 199 350, with 50 rather than 30 [Si(CH₃)₂O] units, was used in place of the organopolysiloxane of example 3. Also for comparative purposes a towel was assessed which had been treated with tap water in place of the fragranced fabric rinse emulsion.

TABLE 2

Softness after treatment with fragranced fabric rinse emulsion

| Active ingredient of fragranced fabric rinse | Softness (max. 45 points) |
|---|---|
| Organopolysiloxane from example 3 | 32 |
| Quaternary polysiloxane according to EP-A 1 199 350* | 34 |
| None | 0 |

*not according to the invention

The experimental results show that using the fragranced fabric rinse emulsion according to the invention on cotton fabric produces a softness which corresponds to the softness obtained with a commercial fabric softener.

All references cited herein are fully incorporated by reference. Having now fully described the invention. It will be understood by one of skill in the art that the invention may be performed within a wide and equivalent range of conditions, parameters and the like, without affecting the spirit or scope of the invention or any embodiment thereof.

What is claimed is:

1. An organopolysiloxane from which a fragrance alcohol can be released, comprising at least one functional group Z having the structure: $-N^+R^1R^2-CH_2-C(O)OY\ A^-$, wherein:

$R^1$ and $R^2$ are mutually independently selected from $C_{1-30}$ alkyl and hydroxyethyl;

Y is the radical of a fragrance alcohol Y—OH; and $A^-$ is the anion of a physiologically compatible acid HA.

2. The organopolysiloxane of claim 1, wherein said organopolysiloxane has a structure according to formula (I):

$$R^3R^4R^5Si-O-CH_2-CH_2-Z \qquad (I)$$

wherein:
R³ is a polysiloxane radical bonded by an oxygen atom;
R⁴ is a $C_{1-30}$ alkyl group or phenyl;
R⁵=R³ or R⁴; and
Z has the same meaning as in claim 1.

3. The organopolysiloxane of claim 1, wherein said organopolysiloxane has a structure according to formula (II):

wherein:
n=3–200;
R⁶=—CH₂—CH₂—N⁺(CH₃)₂—CH₂—C(O)OY A⁻; and
Y and A⁻ have the same meaning as in claim 1.

4. The organopolysiloxane of claim 1, wherein said fragrance alcohol Y—OH is selected from the group consisting of:
4-allyl-2-methoxyphenol (eugenol);
3-(2-bornyloxy)-2-methyl-1-propanol;
2-tert-butylcyclohexanol;
4-tert-butylcyclohexanol;
benzyl alcohol;
1-decanol;
9-decen-1-ol;
dihydroterpineol;
2,4-dimethyl-4-cyclohexen-1-yl methanol;
2,4-dimethylcyclohexyl methanol;
2,6-dimethyl-2-heptanol;
2,6-dimethyl-4-heptanol;
3a,4,5,6,7,7a-hexahydro-2,4-dimethyl-4,7-methano[1H] inden-5-ol;
3,7-dimethyl-1,6-nonadien-3-ol;
2,6-dimethyl-2,7-octadien-6-ol (linalool);
cis-3,7-dimethyl-2,6-octadien-1-ol (nerol);
trans-3,7-dimethyl-2,6-octadien-1-ol (geraniol;
3,7-dimethyl-1,7-octanediol;
3,7-dimethyl-1-octanol (tetrahydrogeraniol);
2,6-dimethyl-2-octanol (tetrahydromyrcenol);
3,7-dimethyl-3-octanol (tetrahydrolinalool);
2,6-dimethyl-7-octen-2-ol (dihydromyrcenol);
3,7-dimethyl-6-octen-1-ol (citronellol);
2,2-dimethyl-3-(3-methylphenyl)-1-propanol;
2,2-dimethyl-3-phenyl-1-propanol, 2-ethoxy-4-methoxymethylphenol;
2-ethyl-4-(2,2,3-trimethyl-3-cyclopenten-1-yl)-2-buten-1-ol;
cis-3-hexen-1-ol, 4-(4-hydroxy-3-methoxyphenyl)-2-butanone;
1-hydroxy-2-(1-methyl-1-hydroxyethyl)-5-methylcyclohexane;
3-(hydroxymethyl)-2-nonanone;
4-(4-hydroxy-4-methylpentyl)-3-cyclohexene-1-carboxaldehyde;
isoborneol;
3-isocamphylcyclohexanol;
2-isopropenyl-5-methylcyclohexanol (isopulegol);
1-isopropyl-4-methylcyclohex-3-enol (terpinenol);
4-isopropylcyclohexanol, 1-(4-isopropylcyclohexyl) ethanol;
4-isopropylcyclohexylmethanol;
2-isopropyl-5-methylcyclohexanol (menthol);
2-isopropyl-5-methylphenol (thymol), 5-isopropyl-2-methylphenol (carvacrol);
2-(4-methyl-3-cyclohexenyl)-2-propanol (terpineol);
2-(4-methylcyclohexyl)-2-propanol (dihydroterpineol);
4-methoxybenzyl alcohol, 2-methoxy-4-methylphenol;
3-methoxy-5-methylphenol;
1-methoxy-4-propenylbenzene (anethol);
2-methoxy-4-propenylphenol (isoeugenol);
4-methyl-3-decen-5-ol;
2-methyl-6-methylene-7-octen-2-ol (myrcenol);
3-methyl-4-phenyl-2-butanol;
2-(2-methylphenyl) ethanol;
2-methyl-4-phenyl-1-pentanol;
3-methyl-5-phenyl-1-pentanol;
2-methyl-1-phenyl-2-propanol;
(1-methyl-(1,2,2-trimethylbicyclo[3.1.0]hex-3-ylmethyl) cyclopropyl) methanol;
3-methyl-4-(2,2,6-trimethylcyclohexen-1-yl)-2-butanol;
2-methyl-4-(2,2,3-trimethyl-3-cyclopenten-1-yl)-2-buten-1-ol;
(3-methyl-1-(2,2,3-trimethyl-3-cyclopentenyl)-3-cyclohexen-1-yl) methanol;
3-methyl-5-(2,2,3-trimethyl-3-cyclopenten-1-yl)-4-penten-2-ol;
2-methyl-2-vinyl-5-(1-hydroxy-1-methylethyl) tetrahydrofuran;
trans,cis-2,6-nonadienol;
1-nonanol;
nopol;
1,2,3,4,4a,5,6,7-octahydro-2,5,5-trimethyl-2-naphthol;
1-octanol;
3,4,5,6,6-pentamethyl-2-heptanol;
2-phenylethanol;
2-phenylpropanol;
3-phenylpropanol (hydrocinnamic alcohol);
3-phenyl-2-propen-1-ol (cinnamic alcohol);
4-(5,5,6-trimethylbicyclo[2.2.1]hept-2-yl) cyclohexan-1-ol;
3,5,5-trimethylcyclohexanol;
2,4,6-trimethyl-4-cyclohexen-1-ylmethanol;
5-(2,2,3-trimethyl-3-cyclopentenyl)-3-methylpentan-2-ol;
3,7,11-trimethyl-2,6,10-dodecatrien-1-ol (farnesol);
3,7,11-trimethyl-1,6,10-dodecatrien-3-ol (nerolidol);
3,5,5-trimethyl-1-hexanol (isononanol);
1-undecanol;
10-undecen-1-ol; and
vetiverol.

5. The organopolysiloxane of any one of claims 1–4, wherein, when dispersed in an an aqueous solution, said organopolysiloxane releases said fragrance alcohol Y—OH more quickly at a pH of 3 than at a pH of 9.

6. A textile treatment agent comprising at least one organopolysiloxane as claimed in any one of claims 1 to 4.

7. A detergent comprising at least one surfactant and at least one organopolysiloxane as claimed in one of claims 1 to 4.

8. A fragranced fabric rinse comprising at least one organopolysiloxane as claimed in any one of claims 1 to 4 in the form of an aqueous dispersion.

9. A personal care product comprising at least one organopolysiloxane as claimed in one of claims 1 to 4.

* * * * *